United States Patent [19]
Marr et al.

[11] Patent Number: 5,486,535
[45] Date of Patent: Jan. 23, 1996

[54] METHOD FOR TREATING TOXOPLASMOSIS

[75] Inventors: J. Joesph Marr, Lake Forest, Ill.; Edward C. Krug, Aurora; Randolph L. Berens, Littleton, both of Colo.; Ou-Yang Ke, Hunan, China

[73] Assignee: Regents of the University of Colorado, Boulder, Colo.

[21] Appl. No.: 117,414

[22] Filed: Sep. 7, 1993

Related U.S. Application Data

[63] Continuation-in-part of Ser. No. 858,226, Mar. 26, 1992, abandoned, which is a continuation of Ser. No. 543,978, Jun. 26, 1990, abandoned.

[51] Int. Cl.⁶ ..................................... A61K 31/335
[52] U.S. Cl. .............................................. 514/450
[58] Field of Search ............................................. 514/450

[56] References Cited

PUBLICATIONS

Chang et al., Translations of The Royal Society of Tropical Medicine and Hygiene, 1988, 82, 867.

*Primary Examiner*—Jerome Goldberg
*Attorney, Agent, or Firm*—Greenlee and Winner

[57] ABSTRACT

This invention provides a method of treating toxoplasmosis in a mammal by administering to the mammal a therapeutically effective dose of an alkyl derivative of qinghaosu. In another embodiment, this invention provides a method for inhibiting the growth of parasites of the suborder Eimeriorina, particularly members of the genus Toxoplasma, by administration of a growth inhibitory level of an alkyl derivative of ginghaosu.

12 Claims, 1 Drawing Sheet

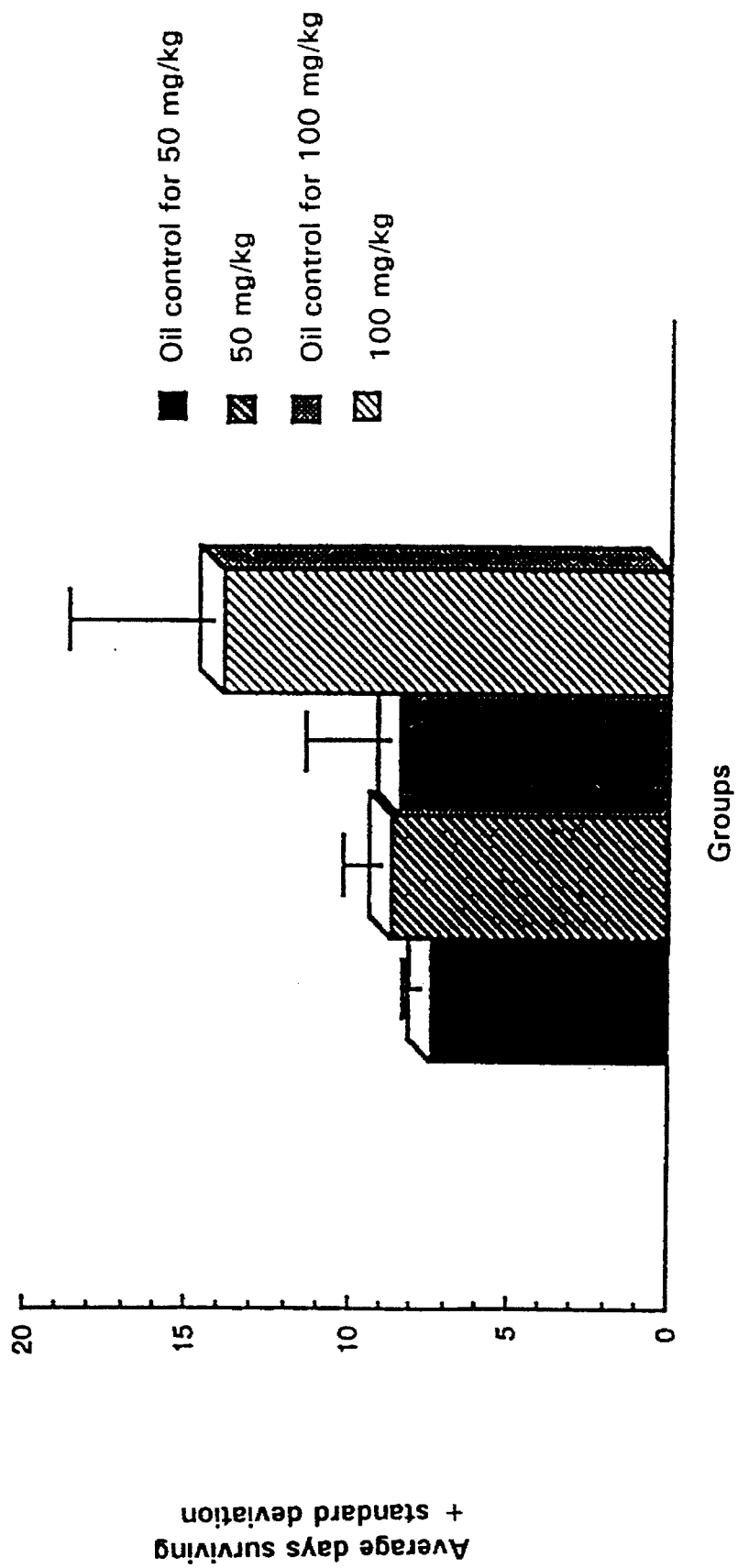

METHOD FOR TREATING TOXOPLASMOSIS

CROSS-REFERENCED TO RELATED APPLICATION

This application is a continuation-in-part application of application Ser. No. 07/858,226, filed Mar. 26, 1992, which is a continuation of application Ser. No. 07/543,978, filed Jun. 26, 1990, both now abandoned.

FIELD OF THE INVENTION

The present invention relates to a method of inhibiting the growth of strains of Toxoplasma and to a method of treating toxoplasmosis by administration of Qinghaosu or certain of its derivatives.

BACKGROUND OF THE INVENTION

*Toxoplasma gondii,* a protozoan parasite, is the causative agent of toxoplasmosis. Although benign in normal individuals, it is a serious problem for immune compromised hosts, such as patients with acquired immune deficiency syndrome (AIDS), and can also cause fetal damage if infection occurs during pregnancy.

The current treatment of choice for toxoplasmosis is the synergistic combination of pyrimethamine with sulfonamides. The toxicity associated with these drugs produces a significant treatment failure in AIDS patients and precludes its use during pregnancy. The motivation to find alternative drugs to combat this parasite is high.

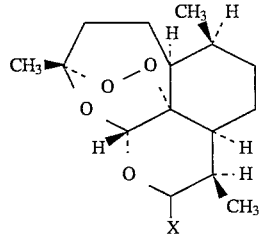

Qinghaosu (QHS) is a sequiterpene lactone natural product derived from the Chinese herb *Artemisia annua* (I, where X=O). *Artemisia annua* has been used for centuries in China as a treatment for fever and malaria (Klayman (1985) Science 228:1049–1055). QHS (also called artemisinine, arteannuin, or artemisinin) has been shown to have in vitro and in vivo activity against Plasmodium (Qinghaosu Antimalaria Coordinating Research Group (1979) Chinese Medical Journal 92:811–816; China Cooperative Research Group on Qinghaosu and Its Derivatives as Antimalarials (1982) Journal of Traditional Chinese Medicine 2:17–24; Jiang et al. (1982) Lancet ii:285; Li et al. (1983) Transactions of the Royal Society of Tropical Medicine and Hygiene 77:522–523; Klayman et al. (1984) Journal of Natural Products 47:715–717).

Although QHS has been shown to have antimalarial activity, it is sparingly soluble in water or oils and is not well absorbed by the gastrointestinal tract. Derivatives with better bioavailability were sought. Dihydroqinghaosu (DHQHS) (I, where X=OH) is the product of reduction of the lactone group of QHS to a lactol (hemiacetal) which is reported to be a mixture of α- and β-epimers. DHQHS is reported to be more effective than QHS against malaria. DHQHS derivatives, substitutions at the OH of DHQHS, have been found to be effective against malaria including alkyl ethers (I, X=OR, where R=alkyl, esters R=CO—alkyl or CO—aryl and carbonates R=CO—O—alkyl or aryl). Additionally, half esters of diacids such as succinate have been found to be effective against malaria. Such esters are prepared as salts i.e., sodium salts. A review of reports of methods used to prepare these derivatives from the natural product QHS is provided in Klayman (1985) Science 228:1049–1055. Artemether is used to refer specifically to the β-epimer of dihydroqinghaosu methyl ether. Similarly the name arteether is used to refer to the β-epimer of dihydroqinghaosu ethyl ether. Artesunate, in contrast, is used to refer to a sodium salt of a hemi succinate of α-dihydroqinghaosu. α and β epimers of derivatives may take different physical forms when isolated in pure form, for example arteether (β-epimer) is reported to be highly crystalline, while the α ethyl ether is reported to be an oil. These differences in physical properties may result in one of the epimers being more easily separated and purified. β- and α-epimers of derivatives may vary in activity, for example it has been suggested in EPO patent application 330,520 that the α-ethyl ether of DQHS is inactive, however it is reported in Brossi et al. (1988 J. Med Chem. 31:645–650) that both the α-ethyl ether and arteether are potent antimalarials.

The mechanism of action of QHS and its derivatives against malaria has not been determined; however, QHS is reported to affect the trophozoite form of the malaria parasite. QHS is also reported to affect polyamine metabolism in the malaria parasite (Geary, et al. (1989) 40:240–244). It has been suggested that QHS acts to inhibit the malaria parasite by generation of active oxygen.

Klayman (1985 Science 228:1049–1055) reports that QHS, artemether, and artesunate are particularly useful for the treatment of patients with cerebral malaria, an advanced form of *Plasmodium falciparum* malaria that can occur when greater than 5% of erythrocytes are infected with parasites. Subsequently, it has been reported that artesunate is sensitive to hydrolysis, making it unclear as to whether the pharmacological effects are due to the parent drug or its hydrolysis product DHQHS (Brossi, et al. (1988) J. Med. Chem 31:645–650). Shwe et al. (1989) Trans. of the Roy. Soc. of Trop. Med. and Hyg. 83:489, report successful treatment of 13 cerebral malaria patients with artemether in combination with another drug.

As antimalarials, dihydroqinghaosu and artemether were reported to be one hundred times more inhibitory to *P. falciparum* than QHS in vitro (Li, et al. (1983) Trans. Royal Soc. Trop. Med. Hygiene 77:522–523) and in vivo in mice (China Cooperative Research Group on Qinghaosu and its derivatives as Antimalarials (1982) and Gu, et al. (1981) Journal of Chinese Medicine 2:17–24; Chung-kuo Yao Li Hsueh Pao 2(2):138–144; Chem. Abstr. 1981, 95:161913b). In mice, artemether was only four times more effective than QHS against *P. berghei* and *P. cynomolgia.* Artemether was reported to be more toxic in mice than QHS (China Cooperative Research Group on Qinghaosu and its derivatives as Antimalarials (1982) Journal of Traditional Chinese Medicine 2:31–38).

Recently, Brossi et al. (1988) J. Med. Chem. 31:645–650 reported arteether and its alpha isomer (alpha-DHQHS ethyl ether) to be potent antimalarials in vitro and in vivo (mice), equipotent with artemether and twice as potent as the natural drug QHS.

Qinghaosu and/or certain of its derivatives have also been reported to be effective in vivo (mice) against the worm *Schistosoma mansoni,* in vivo (rats) against the parasite *Clonorchis sinensis* (Klayman (1985) Science 228:1049–1055), and in vitro against *Naegleria fowleri*, causative agent of primary amebic meningoencephalitis (Cooke et al. (1987) J. Parasit. 73(2):411–413).

In addition, Qinghaosu and certain of its derivatives have been reported variously to be useful for the treatment of systemic lupus erythematosus (Zhuang (1979) J. New Medicine, 6:39), to have virustatic effect on influenza virus and to have an adjuvant effect on cell-mediated immunity as well as an immuno-suppressive effect (Qian et al. (1982) J. Trad. Chin. Med. 2:271).

U.S. Pat. No. 4,816,478 (issued Mar. 28, 1989) of C. R. Thornfeldt claims the use of compositions containing artelinic acid, artemether, artesunate, propyl carbonate dihydroartemisinin, or dihydroartemisinin for the treatment of AIDS or ARC (AIDS related complex).

Chinese patent application No. 85100978 (published Aug. 14, 1986 in Chinese) of Tu et al. is entitled "Reduced artemisinin for malaria and pulmonary trematodiasis treatment." The English abstract of the application suggests that it describes further applications to malaria and the use of reduced artemisinin against lung infection by the trematode Paragonimiasis.

The unique structure of QHS (i.e., the presence of a peroxide linkage) has led researchers to test the activity of endoperoxides and 1,2,4-trioxanes against the malarial parasite. Kepler et al. (1987) Journal of Medicinal Chemistry, 30(8):1505–1509, evaluated several cyclic peroxides for their antimalarial properties. The most active compound synthesized had an $IC_{50}$ of 100 and 57 ng/ml, respectively, for susceptible and resistant strains of *P. falciparum*, as compared to an $IC_{50}$ of less than 3.4 ng/ml against both forms for QHS. The compounds were all inactive in tests for blood schizonticidal activity against *P. berghei*. These compounds were also found to be relatively unstable at ambient temperature. The authors concluded that the peroxide linkage alone is insufficient for antimalarial activity.

Kepler et al. (1988) J. Med. Chem. 31:713–716 synthesized numerous compounds containing the 1,2,4-trioxane ring and tested their antimalarial activity. The authors found that the most active 1,2,4-trioxanes had only the same magnitude of activity as the most active endoperoxides (see Kepler, 1987, supra). These results led the authors to conclude that the 1,2,4-trioxane ring alone is not sufficient for antimalarial activity. Likewise, Jefford et al. (1988) Helvetica Chimica Acta 71:1805–1812, in evaluating the results of the antimalarial activity of their synthesized 1,2,4-trioxanes, concluded that the 1,2,4-trioxane ring itself is necessary, but not a sufficient condition to ensure significant activity. Jefford (EPO Publication No. 286,316, published Oct. 12, 1988 ), however, claims certain synthetic 1,2,4-trioxane derivatives for use in the treatment of tropical diseases such as malaria.

Although the malarial parasite and the toxoplasmosis parasite are both protozoans of the order Eucoccidiorida, the life cycles of these organisms are significantly different. The differences in life cycle between Toxoplasma and Plasmodium are such that a drug that targets a specific stage in one parasite will not necessarily work against the other parasite. Qinghaosu is one such drug that is reported to be specific for the erythrocytic stage of Plasmodium, but has no effect on the liver (exoerythrocytic) stage. One would not expect QHS to work against Toxoplasma because the QHS susceptible life cycle stage in Plasmodium is lacking in Toxoplasma. The presence of a comparable stage of the life cycle is more important than phylogenetic proximity to provide sufficient cause to assume susceptibility to the same compound.

Chang and Pechere (1988) Transactions of the Royal Society of Tropical Medicine and Hygiene 82:867 tested the anti-Toxoplasma activity of arteether. Preliminary results suggested that arteether had some inhibitory effect on Toxoplasma replication at levels as low as 0.1 µg/ml in in vitro assays using unelicited mouse peritoneal macrophages. However, the authors stated that these results were not reproducible. They further report that arteether had no inhibitory effect on the incorporation of labelled uracil by intracellular *T. gondii* up to concentrations of 400 µg/ml. In addition, subcutaneous administration of arteether to mice infected with *T. gondii* was reported to be ineffective therapy for toxoplasmosis. Daily doses of 200 mg/kg were noted to increase survival time significantly, but that the treated mice eventually died of toxoplasmosis. It is also noted that arteether levels of 400 and 600 mg/kg were toxic to the animals treated. The authors concluded that arteether would not be useful in the treatment of toxoplasmosis.

Three synthetic 1,2,4-trioxanes (pentatroxane, thiahexatroxane, and hexatroxanone) have been tested for their in vitro activity against *T. gondii* (Chang et al. (1989) Antimicrobial Agents and Chemotherapy 33(10):1748–1752). The activities of the synthetic 1,2,4-trioxanes against intracellular *T. gondii* were assessed by [$^3$H] uracil incorporation. All three 1,2,4-trioxanes inhibited [$^3$H] uracil incorporation by infected macrophages. They were as effective as pyrimethamine and pyrimethamine in combination with sulfadiazine in inhibiting intracellular *T. gondii*. When their ability to reinfect macrophages was tested, however, none of the trioxanes affected the viability of extracellular *T. gondii*. Thus, the synthetic 1,2,4-trioxanes were able to block the nucleotide synthesis of the intracellular parasites, but were unable to affect viability of extracellular *T. gondii*.

SUMMARY OF THE INVENTION

This invention is based on the finding that in vitro plaque formation of *Toxoplasma gondii* was inhibited by the compound qinghaosu and certain of its derivatives.

It is believed that this is the first report of effective inhibition of *Toxoplasma gondii* by QHS, dihydroqinghaosu (DHQHS), and alkyl ether derivatives.

This invention provides a method for inhibiting the growth of *Toxoplasma* spp., particularly *Toxoplasma gondii* in vitro and in vivo by administration of a growth inhibitory level of QHS, DHQHS or a derivative thereof to the growth environment of the parasite.

This invention further provides a method of treating toxoplasmosis in a mammal by administering to the mammal a therapeutically effective dose of QHS, DHQHS or its alkyl ether derivatives.

More specifically, the therapeutic method of the present invention involves administration of a therapeutically effective amount of QHS, DHQHS or an alkyl ether derivative thereof (I where X=OR and R is an alkyl group having one to six carbon atoms) to a mammal having toxoplasmosis.

QHS, DHQHS and the alkyl ethers (I) where X=OR and R is methyl, ethyl, isopropyl and, isobutyl are more preferred toxoplasmosis therapeutic agents. Of the DHQHS ether derivatives the methyl and ethyl ethers, including artemether and arteether are most preferred.

QHS (I, X=O), DHQHS (I, X=OH) and alkyl ether derivatives of DHQHS (I, where X=OR, R=alkyl group having 1 to 6 carbon atoms) are preferred agents for inhibition of growth of Toxoplasma.

More preferred growth inhibitory agents are QHS, DHQHS, and the alkyl ether derivatives (I), where X=OR and R is methyl, ethyl, i-propyl and i-butyl groups. Of the DHQHS ether derivatives the methyl and ethyl ethers including artemether and arteether are most preferred.

BRIEF DESCRIPTION OF THE DRAWING

FIG. 1 is a graph showing increase of survival time of *T. gondii* infected mice treated with artemether.

DETAILED DESCRIPTION OF THE INVENTION

The present invention provides a method of inhibiting the growth of *Toxoplasma spp.* and of treating toxoplasmosis by administration of QHS and certain of its derivatives. Toxoplasmosis includes all of the side-effects or symptoms produced as a result of an infection by *Toxoplasma gondii* or other strains of Toxoplasma causing like infections.

*Toxoplasma gondii* is the species most often associated with toxoplasmosis, but other species of Toxoplasma may be associated with the condition. QHS and certain of its derivatives would likewise be effective against all such species.

Growth inhibition by QHS and its derivatives and the effectiveness of such compounds for treatment of toxoplasmosis are assessed herein by in vitro growth inhibition assays as described herein. QHS and derivatives thereof found to exhibit growth inhibition of Toxoplasma strains in such in vitro assays are effective for inhibition of Toxiokasna strains in vivo, i.e., specifically in a natural growth environment of the parasite such as in a living organism. In vivo results showing the usefulness of certain derivatives of QHS are also presented herein.

QHS and its derivatives which are demonstrated to inhibit the growth of *Toxoplasma gondii* in in vitro plaque assays, and are effective for treatment of toxoplasmosis in individuals having that condition.

Qinghaosu and its derivatives, specifically, dihydroqinghaosu (DHQHS), artemether (methyl-ether-QHS), arteether (ethyl-ether-QHS), i-propyl-ether-QHS, i-butyl-ether-QHS, and sec-butyl-ether-QHS are herein shown to have an inhibitory effect on the growth of *T. gondii* plaques in vitro (Table 1). QHS and certain of its derivatives were known to be effective against the malaria parasite Plasmodium. The results presented herein are surprising and unexpected because of the differences in life cycles of Plasmodium and Toxoplasma, and especially in view of the previously reported failure of certain QHS derivatives (arteether) to inhibit *T. gondii* (Chang et al. 1988 supra).

In in vitro plaque assays using a range of QHS concentrations, the *T. gondii* parasite was inhibited by QHS at 0.23 μg/ml and eliminated by 0.4 μg/ml. The number of plaques is expressed as a percentage of the matched DMSO-treated control cultures. QHS at 0.23 μg/ml allowed growth of 7 to 10 parasites per injection site but insufficient damage occurred to produce a macroscopic plaque. At higher concentrations neither plaques nor sites of *T. gondii* growth were found. DMSO did not stop plaque formation even at the highest concentrations (0.6%) used with QHS. However, DMSO concentrations above 1.6% interfered with the plaque assay and at 10% caused release of intracellular *T. gondii* within fifteen minutes. Gu et al. (1983, Biochemical Pharmacology 32:2463–2466) suggests that the mechanism of action of QHS involves the inhibition of protein synthesis based on the finding that the drug stops [$^3$H]-isoleucine incorporation by *Plasmodium falciparum* within one hour after administration.

The antitoxoplasmic activity of QHS on *T. gondii* was shown to be by direct action. Pretreatment of fibroblasts with QHS had no effect. Fibroblasts were treated with QHS for daily intervals up to five days. The drug was removed prior to infection. The cells supported *T. gondii* growth at levels comparable to untreated controls.

Pretreatment of *T. gondii* with QHS caused a reduction in plaque size. *T. gondii* were pretreated with QHS at 4 μg/ml and 0.4 μg/ml. The concentrations were chosen to greatly exceed (4 μg/ml) or slightly exceed (0.4 μg/ml) the effective concentrations of QHS. Pretreatment with either concentration of QHS for two hours had no effect on the growth of *T. gondii*. However, exposure to QHS for four hours at 4 μg/ml and sixteen hours at both concentrations is detrimental to the parasite, as evidenced by reduced plaque size.

Thus, the results of the pretreatment of fibroblasts with QHS and pretreatment of *T. gondii* with QHS suggest that antitoxoplasmic activity of QHS on *T. gondii* is by direct action. That is, QHS works directly on effecting the parasite, and does not work indirectly by causing the fibroblasts to be less hospitable.

The effectiveness of QHS and its derivatives for inhibition of *T. gondii* growth are presented in Table 1. At about 1 μg/ml QHS, DHQHS, i-propyl-ether-QHS and i-butyl-ether-QHS were able to prevent macro and microscopic evidence of parasite growth. At about 0.1 μg/ml, QHS, DHQHS and i-propyl-ether-QHS were able to reduce the size and the number (as given as a percentage of the matched DMSO group) of plaques formed. i-butyl-ether-QHS at about 0.1 μg/ml was able to reduce the size of the plaques. Methyl-ether-QHS, ethyl-ether-QHS and sec-buty-ether-QHS inhibited all indices of growth at ten-fold lower concentrations; however, some Toxoplasma was seen upon microscopy for ethyl-ether-QHS and sec-butyl-ether-QHS.

Infected fibroblasts were incubated for up to 27 days with QHS. All infected fibroblasts not treated with drugs or treated with qinghaosu at 0.4 μg/ml were destroyed by 14 days. Qinghaosu at 1.3 μg/ml reduced *T. gondii* plaque number from too numerous to count after 5 days to 13 plaques per 25 cm$^2$ culture of fibroblasts after 14 days. Treatment of infected flasks for an additional 8 days (22 days total) resulted in complete elimination of the *T. gondii* infection as shown by lack of parasite plaque formations during subsequent subculture in drug-free medium. QHS treatment at 4.0 μg/ml did not stop *T. gondii* replication and plaque formation within 5 days; however, by 14 days it eliminated *T. gondii* infection by the same criteria. The morphology and growth of the fibroblasts during the treatment with QHS was normal throughout the experiment. Thus, complete elimination of *T. gondii* was achieved with QHS at ≧1.3 μg/ml and longer treatment. Higher QHS concentrations reduced the treatment time necessary to produce *T. gondii* clearance.

The concentration of QHS necessary to eliminate *T. gondii* from long term culture (1.3 μg/ml) was considerably higher than that necessary to prevent plaque formation (0.4 μg/ml). Thus, experiments were conducted to determine the influence of serum in the medium and growing host cells on QHS. The cells were grown on media containing either 0.3% albumin or 10% serum. In the presence of 10% serum (vs. 0.3% albumin) the effectiveness of QHS was reduced. It was found that the presence of 10% serum in place of 0.3% albumin both reduced the plaque amount by 25% in infection control cultures as well as reduced the efficiency of QHS at 0.1 µg/ml by one scoring unit (* vs.+, as defined by the scoring system in Table 1).

The concentration that eliminated plaques, however, was identical for both media formulations. Plaque size was identical for both albumin and serum in the non-drug control groups.

A reduction in number of plaques by serum has been previously reported by Doran (1973, in *The Coccidia, Eimeria, isospora, toxoplasma, and related genera*, Hammond and Long (eds.) University Park Press, pp. 183–252) who states that serum is inhibitory to *T. gondii* penetration of host cells. The apparent reduction in QHS effectiveness by serum is consistent with the poor water solubility of QHS and its tendency to bind to serum proteins which would reduce its bioavailability. The binding of the artemether derivative of QHS to serum protein has been reported to be 58% in mice, 61% in monkeys and 77% in humans (China Cooperative Research Group on Qinghaosu and its derivatives as antimalarials (1982) Journal of Traditional Chinese Medicine 2:17–24; China Cooperative Research Group on Qinghaosu and its derivatives as Antimalarials (1982) Journal of Traditional Chinese Medicine 2:25–30).

Fibroblast growth status had no effect on drug concentrations that visibly stopped parasite growth. Visible parasite growth was stopped by QHS at 1 µg/ml in both growing and non-growing fibroblast cultures.

Pyrimethamine was sufficiently toxic to fibroblast growth in the long term drug treatment study that confluent cultures were not achieved in the same time that QHS treated fibroblasts were subcultured three times. Even upon removal of pyrimethamine and several washes with fresh medium, suppression of fibroblast growth persisted for over 10 days; inhibition was the same at 10 and 1 µg pyrimethamine per ml. In contrast, QHS eliminated *T. gondii* at concentrations that caused no apparent cytotoxicity to host cells. These results indicate that QHS or a derivative thereof represents a less toxic alternative to pyrimethamine as an antitoxoplasmic agent.

The methods for preparing artemether, DHQHS, and arteether, are described in EPO Publication No. 330,520 by Peter Buchs, published Aug. 3, 1989; Brossi et al. (1988) J. Med. Chem. 31:645–650). Other alkyl derivatives can be readily made by appropriate modification of known methods (e.g., those described in Brossi et al. (1988) supra) employing readily available starting materials.

QHS has low solubility in most solvents that can be administered to man and is not well absorbed by the gastrointestinal tract (Peters et al. (1986) Annals of Tropical Medicine and Parasitology 80:483–489). Experiments have been carried out to determine the most suitable vehicle and route for its administration in vivo (Klayman, supra). In addition, researchers have attempted to synthesize QHS derivatives with improved bioavailability. To determine the most effective vehicle and mode of administering QHS and its derivatives to *T. gondii* patients, it would be known to one of ordinary skill in the art to try various pharmaceutical formulations (e.g. tablet, oil, oil suspension, water) and administrations (e.g. oral, intramuscular, intravenous).

Further, toxicity studies have been performed and show that QHS is relatively safe (Klayman, supra). Dosage needed can be determined experimentally employing information about toxicity and effective dosage for applications to malaria treatment. Thus, dosage will depend on form and site of infection. Dosage will depend on formulation and type of administration of drug. For example, bioavailability of compounds may be lower when administered orally in comparison to administration by injection.

The action of QHS and its derivatives was found to be rapid in patients treated for malaria, but patients experienced recrudescence and required a supplemental drug (Klayman, supra). It would be known to one of ordinary skill in the art to try various doses and combinations of QHS and/or its derivatives alone or in combination with other antitoxoplasmic compounds to obtain the fastest recovery from toxoplasmosis with the least amount of recrudescence. It is possible that QHS may act synergistically when used in combination with other antitoxoplasmic drugs.

It will be apparent to those in the art to take into account factors such as age, weight and sex when determining an appropriate dose.

Taxonomically, *Toxoplasma gondii* is in the subkingdom Protozoa, phylum Ampicomplexa, class Sporozoasida, subclass Coccidiasina, order Eucoccidiorida, and suborder Eimeriorina. Other members of the suborder Eimeriorina, such as parasites from the genera Cryptosporidium, Eimeria, Isospora, and Sarcocystis, can be inhibited by QHS and its derivatives, as these organisms have similar life cycles. Members of the suborder Eimeriorina are described as having micro- and macrogametes that develop independently (no syzygy); zygotes are nonmotile; oocysts are present; and the sporozoites are enclosed in sporocysts.

Their trophozoites (vegetative protozoan) are mostly nonmotile and usually intracellular, and often show a rapid loss of the apical complex and the two inner membranes after entering host cells, where they reside within a parasitophorous vacuole. This appears identical with a phagocytic vacuole, but the parasite apparently evades digestion. Each female gamont produces a single female gamete, and gamonts of the two sexes undergo gametogenesis without encystment, and usually before meeting together; they are usually oogamous with small flagellated male gametes.

Cryptosporidium species cause diarrheal illness in several animal species, including humans. In healthy, immunocompetent persons the clinical symptoms and oocyst shedding generally resolve spontaneously; however, the symptoms are severe. Cryptosporidium causes a cholera-like illness in immunedeficient patients, especially those with AIDS. The symptoms can become progressively worse with time in immunocompromised individuals, and may be a major factor leading to death. Further, in addition to causing infection of the gastrointestinal tract, Cryptosporidium may cause infections of the biliary tree, gall bladder epithelium, and respiratory tract in immune compromised individuals. Thus, there is a need for effective therapy to treat: the disease, as none currently exists. QHS and its derivatives found to be inhibitory to Cryptosporidium in vitro are useful for treatment of infections caused by Cryptosporidium in individuals having such conditions.

Other closely related organisms with similar life cycles include members of the genus Eimeria. For example, *Eimeria steidae* causes severe hepatitis of rabbits and can be fatal. Other species of Eimeria are pathogenic in various domestic animals such as chickens and cattle. QHS and its derivatives found to be inhibitory to Eimeria in Vitro are useful for treatment of infections caused by Eimeria in individuals having such conditions.

Isospora can be an infectious agent in domestic animals and man. QHS and its derivatives found to be inhibitory to Isospora in vitro are useful for treatment of infections caused by Isospora in individuals having such conditions.

Sarcocystis can be an infectious agent in mammals including dogs, sheep and man. QHS and its derivatives found to be inhibitory to Sarcocystis in vitro are useful for treatment of infections caused by Sarcocystis in individuals having such conditions.

Growth inhibition by QHS and its derivatives and the effectiveness of such compounds for treatment of the diseases caused by Cryptosporidium, Isospora, Eimeria and Sarcocystis are assessed herein by in vitro growth inhibition assays as described in Example 2, or by methods generally known in the art. QHS and derivatives thereof found to exhibit growth inhibition of Cryptosporidium, Isospora, Eimeria, and Sarcocystis species in such in vitro assays are effective for inhibition of these species in vivo, i.e., in a natural growth environment of the parasite such as in a living organism. Specifically, QHS and its derivatives demonstrated to inhibit growth of Cryptosporidium, Isospora, Eimeria and Sarcocystis in in vitro assays are effective for treatment of diseases caused by these organisms in individuals having the diseases.

The following examples are included for illustrative purposes only and are not intended to limit the scope of the invention.

EXAMPLE 1

The RH strain of *Toxoplasma gondii* was obtained from J. D. Schwartzman from the University of Virginia Medical School at Charlottesville, Va. (originally from E. R. Pferrerkorn). The strain is publicly available through recognized depositories. The strain was maintained in locally obtained human embryonic lung fibroblasts of passage less than 30. The fibroblasts were grown in VA-13 medium (Minimal Essential Medium with Earl's salts, 2× MEM essential amino acids, 1× MEM non-essential amino acids, 2× MEM vitamins, 3× glucose, 1 mM Na pyruvate, 100 units/ml penicillin G, and 100 μg/ml streptomycin sulfate), pH 7.2. VA-13 medium was supplemented with 10% adult bovine serum for growth of non-parasitized fibroblasts. For growth of *T. gondii* in stationary phase fibroblasts, VA-13 was used with 0.3% bovine serum albumin, (Cohn fraction V). When both the fibroblasts and *T. gondii* were simultaneously grown, the VA-13 medium was supplemented with fetal bovine serum (10%). All cultures were incubated in 5% $CO_2$, 95% air at 37° C.

Fetal bovine serum was obtained from Hyclone (Logan, Utah). Culture plastic ware were from Corning (Littleton, Colo.). All other culture media were from Sigma Chemical Company (St. Louis, Mo.), and the remaining reagents were of analytical grade.

Quantitation of QHS and its Derivatives.

Qinghaosu (artemisinin), dihydroqinghaosu (dihydroartemisinin), and artemether (methyl-ether-QHS) arteether (ethyl-ether-QHS), 1-propyl-ether-QHS, 1-butyl-ether-QHS, and sec-butyl-ether-QHS were obtained from Hauser Chemical Research, Inc. (Boulder, Colo.). The compounds were dissolved in DMSO (dimethylsulfoxide) at 3 mg/ml. The concentration of QHS was verified using the Method of Zhao and Zeng (Zhao, et al. (1986) Anal. Chem. 58:289–292). One part QHS solution was mixed with 4 parts 50 mM NaOH and heated for 30 mirLutes at 45° C. The mixture was rapidly cooled to room temperature and 5 parts of 100mM acetic acid in 20% ethanol was added. The final reaction mixture was diluted 1/20 with 20 mM potassium phosphate buffer at pH 6.0 and the optical density measured at 259 nm using a Beckman DU-7 Spectrophotometer. The control used for the spectrophotometer was the DMSO solvent processed in parallel. The extinction coefficient used was $1.3 \times 10^4$ L/(mol cm) (Zhao, et al. (1986) Anal. Chem. 58:289–292).

The derivatives were quantitated by weight and dissolved in DMSO similar to QHS.

EXAMPLE 2

Plaque assay.

The plaque assay is based on the method of Schwartzman (Schwartzman, J. D. (1986) Infection and Immunity 51(3):760–764) and Chaparas and Schlesinger (Chaparas, S. D., R. W. Schlesinger (1959) Proc. Soc. Exp. Biol. Med. 102:431–437). Fibroblasts were inoculated into twelve well culture plates and allowed to grow to confluence. Three days after confluence the fibroblast monolayers were infected with 200 *T. gondii* per well to give an inoculum of 1 parasite per 1000 fibroblasts. Unless otherwise indicated the parasites were incubated with the fibroblasts for three hours before addition of the drug. In each assay two parasitized culture wells per group received either: 1) a no drug control; 2) 10 μg/ml pyrimethamine to kill *T. gondii* as procedure control (Cook, M. K., and L. Jacobs (1958) J. Parasit. 44:280–288); 3) QHS at test concentrations; or 4) DMSO at the concentration found in the matched QHS wells. The culture plates were incubated for five days in a humidified chamber in standard culture conditions without being moved so that distinct plaques were formed. The cultures were then examined by phase contrast microscopy to assess the condition of the fibroblasts and the *T. gondii*. The old media were decanted and the cultures were fixed with methanol for 5 minutes, air dried and the plaques counted with the aid of an American Optical darkfield Quebec colony counter. The plaque size was quantitated on a "four +" scale. Four plus is the size of the control plaques. Three plus is a plaque diminished in size, but larger than half size, which is two plus. One plus is a barely visible plaque.

For microscopic visualization of fixed *T. gondii* the fixed fibroblast monolayers were stained for 30 min with a 1:50 dilution in distilled water of Giemsa stain (Harleco, Gibbstown, N.J.).

Effectiveness of QHS derivatives on *T. gondii*.

The qinghaosu derivatives dihydroqinghaosu, artemether and other derivatives were tested for inhibition of plaque formation by *T. gondii* by the same method used for QHS. The dose-response titrations of qinghaosu and its derivatives are compared in Table 1.

EXAMPLE 3

Fibroblasts preincubation with QHS.

A series of fibroblasts culture plates were allowed to grow to confluence at which time one culture plate received QHS in the appropriate wells for each of 5 consecutive days. After five days the QHS was removed and 200 *T. gondii* were added per well. After five additional days the results were scored as described in Example 2.

*T. gondii* preincubation with QHS.

From a population of free fresh *T. gondii* two hundred parasites were added per well to three culture wells containing fibroblasts to serve as time zero controls. The remaining parasites were divided into five groups and stored at 37° C. in VA-13 with 0.3% albumin in standard culture conditions. One group each received QHS at 4 or 0.4 µg/ml, DMSO at 0.1% or 0.01%, or no drug. At 2 and 4 hours 200 parasites and at 16 hours 400 parasites were added from each group to fibroblast cultures. This form of *T. gondii* gradually dies as it remains outside of host cells and by phase microscopy becomes less refractive and more rounded than live parasites. The transition from live to dead *T. gondii* is not sufficiently crisp that only live organisms can be counted with certainty. Therefore, a larger number of parasites (four hundred) with normal morphology were used of those pretreated with QHS for 16 hours. One hundred and twenty hours after the addition of *T. gondii* the cultures were terminated and quantitated as above.

EXAMPLE 4

Abolition of an established infection.

The ability of QHS to abolish an established infection of *T. gondii* was determined using a modification of the procedure of Berens et al. (1982, Antimicrob. Agents Chemother. 22(4):657–661). A confluent fibroblast monolayer in a 150 cm$^2$ culture flask was infected with 6400 *T. gondii* (approximately 1 *T. gondii* per 5000 fibroblasts). After three days of growth the infected fibroblast monolayer was trypsin treated and the suspended fibroblasts subcultured at one fourth the cell density in 25 cm$^2$ culture flasks. The infected fibroblasts were allowed to adhere for approximately 18 hours (overnight). Time zero was defined as this point and treatment was initiated on duplicate flasks for each treatment group. Also, at time zero, two flasks were fixed in methanol and stained with Giemsa to determine the initial percentage of infected fibroblasts. Five experimental groups were used. Three groups received QHS at either 0.4, 1.3 or 4.0 µg/ml. One group received drug-free culture medium, and the final culture received pyrimethamine at 10 µg/ml.

These cultures were allowed to grow for 5 days and then they were subcultured at one fourth the cell density. The procedure and treatment of subcultures of drug treated cultures was constant throughout this experiment. One subcultured flask continued with uninterrupted drug exposure; a second flask was allowed to grow drug-free; a third flask was maintained with drug for several hours at 37° C. while the fibroblasts attached and then fixed and stained as above to determine percentage of host cells infected. The cultures that continued to receive drug exposure were allowed to grow to confluence at which time they were again subcultured into the three groups described above. This process was repeated until the flasks of that drug concentration were terminated as described below.

The subcultures that ceased receiving drug exposure were repeatedly allowed to grow to confluence and be subcultured into two flasks at a one-to four dilution. One of these two cultures was fixed and preserved as above; the other was continued in drug-free medium. When any drug-free group was subcultured for four times with no evidence of *T. gondii* all flasks associated with that drug concentration were terminated. The infected fibroblast cultures that received no drug treatment were continued and subcultured in the absence of treatment until the host cells were destroyed by the parasite.

All flasks were subcultured in synchrony throughout the experiment except the pyrimethamine treated group which after 14 days of drug treatment was growing at a much slower rate. The culture medium was not changed for the initial 5 days of this experiment but was changed every third day in all flasks for the rest of the experiment.

The long-term fibroblast cultures differ in at least two ways from the plaque assays. First, they contain actively growing fibroblasts rather than stationary phase fibroblasts, and second, the incubation medium contains 10% serum instead of 0.3% albumin. To determine the effects of serum on QHS effectiveness, confluent monolayers of fibroblasts in culture wells received either albumin or serum and were then infected with *T. gondii* at 200 parasites per well. Within three hours the appropriate drugs were added and after five days the cultures and plaques were quantified as above. To determine the effectiveness of QHS on parasite growth in actively replicating versus non dividing host cells, confluent fibroblasts were subcultured at a 1 to 5 dilution in culture wells. Three hours later these wells and a set of culture wells containing confluent, non-dividing fibroblasts received 200 *T. gondii* per well and the appropriate drugs in 10% serum. The cultures were incubated for 5 days and then examined as above. Results are described hereinbefore.

EXAMPLE 5

In vivo efficacy of qinghaosu (QHS) against *Toxoplasma gondii*.

A 60 mg/ml stock suspension of QHS was prepared in soybean oil. Toxoplasma-infected mice were treated at a concentration of 150 mg/kg body weight/day by subcutaneous injection (0.05 ml) given once daily. Thirty mice (Swiss whites) were randomly divided. into 3 groups of 10. The test groups were: 1) toxoplasma infected, QHS/oil treated; 2) toxoplasma infected, non-QHS/oil controls; and 3) uninfected, QHS/oil treated controls. Mice were infected with 2×10$^3$ *T. gondii* tachyzoites (the highly virulent RH strain) by intraperitoneal injection. Two hours after infection treatment was started. The following results were obtained:

| Day (post-infection) | Mice Alive in Group | | |
|---|---|---|---|
| | 1 | 2 | 3 |
| 1 | 10 | 10 | 10 |
| 2 | 10 | 10 | 10 |
| 3 | 10 | 10 | 10 |
| 4 | 10 | 10 | 10 |
| 5 | 10 | 10 | 10 |
| 6 | 8 | 10 | 10 |
| 7 | 7 | 6 | 10 |
| 8 | 2 | 1 | 10 |
| 9 | 1 | 1 | 10 |
| 10 | 1 | 0 | 10 |
| 11 | 1 | 0 | 10 |
| 12 | 1 | 0 | 10 |
| 13 | 1 | 0 | 10 |
| 14 | 0 | 0 | 10 |

Group 1: Infected QHS treated mice
Group 2: Infected nondrug control mice
Group 3: Uninfected QHS treated control mice
Days 1 to 5 post-infection: The mice in all groups appeared normal.

Group 1: Infected QHS treated mice Group 2: Infected nondrug control mice Group 3: Uninfected QHS treated control mice Days 1 to 5 post-infection: The mice in all groups appeared normal.

Day 6: Two of the QHS treated infected mice died. The drug control group appeared normalas did the remaining drug treated mice. All infected non-drug control mice appeared lethargic compared to the other two groups.

Day 7: Four of the infected non-drug control mice died as well as one of the infected QHS treated mice. The QHS treated mice on day 6 and 7 appeared much less lethargic compared to the infected non-treated controls.

Day 8: Five mice died in both the infected QHS treated group and the infected non-drug control group.
Day 9: An infected QHS treated mouse died.
Day 10: The last infected non-drug control mouse died. Treatment was stopped.
Day 14: The last infected QHS treated mouse died. All the QHS treated uninfected control mice appeared normal.

Autopsy of the uninfected drug control mice revealed a low amount of a QHS/oil suspension in the subcutaneous space. This suggested that a significant amount of the drug in the infected treated mice was not absorbed and that toxoplasma was exposed to a lower drug concentration than expected. Thus, a second experiment was performed using a different delivery vehicle and twice the daily dosage. A summary of the experiment and results follows.

A 30 mg/ml stock suspension was prepared in DMSO/ soybean oil (1:1). Mice were treated at a concentration of 300 mg/kg body weight/day given in two divided dosages by subcutaneous injection (0.1 ml per injection). Mice were divided into two groups of 9 mice and one group of 3 mice. One group of nine mice served as the infected treated group, the other group served as the infected non-drug oil/DMSO control group. The group of 3 mice was the uninfected treated control group. Because a limited number of mice were available due to budget constraints, the infected treated group consisted of the uninfected drug controls from the first experiment. This experiment was started 21 days after the termination of the first experiment. Drug treatment was started 3 days before infection. Mice were infected with $2 \times 10^3$ T. gondii tachyzoites (the highly virulent RH strain) by intraperitoneal injection. The following results were obtained:

| Day (post-infection) | Mice Alive in Group | | |
|---|---|---|---|
| | 1 | 2 | 3 |
| 1 | 9 | 9 | 3 |
| 2 | 9 | 9 | 3 |
| 3 | 9 | 9 | 3 |
| 4 | 8* | 9 | 3 |
| 5 | 8 | 8* | 3 |
| 6 | 8 | 7 | 3 |
| 7 | 8 | 6 | 2* |
| 8 | 6* | 1 | 2 |
| 9 | 4* | 0 | 2 |
| 10 | 2 | 0 | 2 |
| 11 | 1 | 0 | 2 |
| 12 | 0 | 0 | 2 |

*Mouse died from apparent trauma from injection

Group 1: Infected QHS treated mice Group 2: Infected nondrug control mice Group 3: Uninfected QHS treated control mice Days 1 to 3 post-infection: All mice were noticeably skittish.
Day 4: One of the infected treated mice died from needle laceration to the kidney immediately after injection.
Day 5: There was a noticeable difference between infected treated mice and infected non-drug control mice, which were very lethargic compared to the other two groups. One of the infected non-drug control mice died, probably due to injection trauma.
Day 6: One of the infected non-drug control mice died. The infected treated mice were much more active compared to the infected non-drug controls.
Day 7: One infected non-drug control mouse and one uninfected treated control mouse died. Autopsy of the former showed the presence of toxoplasma in a touch preparation of the peritoneal fluid; there was no indication of needle trauma. The uninfected drug control mouse died from apparent needle trauma.
Day 8: Five infected non-drug control mice died. All were positive for toxoplasma in touch preparations of the peritoneal fluid. There was no indication of needle trauma. Two infected treated mice died immediately after drug injection apparently from needle laceration to the kidneys. Peritoneal touch preparation showed no indication of toxoplasma.
Day 9: Two infected treated mice died from apparent needle laceration to a kidney; a few parasites were detected in one of the mice, none in the other. The last of the infected non-drug control mice died; many parasites were present in the peritoneal fluid. Because of the loss of mice due to needle trauma, injections were stopped.

Up to day 9, five infected treated mice were dead, one uninfected drug control mouse was dead, and all of the infected non-drug control mice were dead. All the infected treated mice showed evidence of trauma from the injection and only one of these was positive (at a low level) for toxoplasma in peritoneal touch preparations. Of the nine infected non-drug mice that died, only three showed any evidence of needle trauma, and all but one was positive for toxoplasma. The one uninfected treated control mouse that died showed evidence of needle laceration to the kidney.

Day 10: Two of the infected treated mice died; there was no evidence of needle trauma and both were positive for peritoneal toxoplasma.
Day 11: One infected treated mouse died and had a small number of peritoneal parasites.
Day 12: The last infected treated mouse died. It was positive for toxoplasma. The two remaining uninfected drug control mice appeared normal.

Based on the results of the experiments presented above, the following conclusions can be made. QHS at 150 mg/kg body weight in oil apparently does not cause toxicity in mice. QHS at 300 mg/kg body weight in oil/DMSO (1:1) apparently does not cause toxicity in mice. These results are promising and show that QHS delays the onset of toxoplasmosis in mice. On day 9 of the second experiment, the last day of drug treatment, 45% of infected drug treated mice were alive, while none of the infected non-drug controls were alive. However, if the deaths of the infected treated mice that died up to day 9 were due to needle trauma, as is believed true based on autopsy results, then on day 9 there would have been a 100% survival of the infected treated mice compared to 0% survival of the infected non-drug control mice. As discussed above, only one of the infected treated mice that had died up to day 9 showed signs of toxoplasmosis. Once treatment with QHS was withdrawn, however, the remaining infected mice died. All of these mice tested positive for toxoplasma.

In the first experiment it was determined that the drug in the injected treated mice was not absorbed properly, suggesting that an effective concentration of the drug was not present. (This was the motivation for performing the second experiment.) In the second experiment, there were a high number of infected treated mice that died due to needle trauma. Several factors could have contributed to this: 1) these mice were much less lethargic compared to the infected non-drug control mice; and 2) this group of mice consisted of the uninfected drug controls from the previous experiment and were much more skittish during injection, probably due to prior experience with the injection discomfort. It is also possible that the presence of the DMSO in the injection mixture increased the amount of discomfort compared to oil alone as used in the first experiment.

EXAMPLE 6

In vivo tests of artemether against Toxoplasma gondii.

Female ICR strain mice (from SASCO Inc.) were weighed, injected IP with 200 fresh *Toxoplasma gondii*, and segregated into experimental groups. Three hours later the mice received their first injection of 50 microliters of peanut oil, either with or without methyl-ether quinghaosu (artemether). Thereafter, they were injected morning and evening with 50 microliters of the appropriate solution for a total of 100 microliters of oil per day. Oil was formulated with artemether to yield doses of 50 or 100 mg/kg for the different studies. Mice in the study of 50 mg/kg artemether had an average weight of 23.0 grams. The mice receiving 100 mg/kg per day artemether averaged 25.7 grams.

The survival times of mice in the different groups are presented in FIG. 1. The infected mice receiving 50 mg/kg artemether started to die on the same day as those not receiving artemether; however, the longest-lived treatment mouse survived 50% longer than the longest-lived nonartemether-treated mouse. Treatment with 100 mg/kg artemether produced a 64% increase in survival in treated mice compared to control mice. When the survival results were analyzed for both treatment protocols using the t-test it was found that the increased survival of artemether-treated mice was significant at a probability of less than 0.025 for both groups.

It is intended that this invention be limited only by the spirit and scope of the appended claims.

TABLE 1

Effects of QHS and derivatives on *T. gondii* plaques.

| Drug (μg/ml) | 10 | 1 | 0.1 | 0.01 |
|---|---|---|---|---|
| QHS | 0 | 0 | 89(++) | 104(++++) |
| Dihydro-QHS | 0 | 0 | 76(++) | 101(++++) |
| Methyl-ether-QHS | 0 | 0 | 0 | 98(+) |
| Ethyl-ether-QHS | 0 | 0 | 0* | 119(++++) |
| i-propyl-ether-QHS | 0 | 0 | 50(++) | 100(++++) |
| i-butyl-ether-QHS | 0 | 0 | 124(+++) | 100(++++) |
| Sec-Butyl-ether-QHS | 0 | 0 | 0* | 86(++++) |

Size of plaques are expressed on a 4 plus scale.
++++ is normal size plaque
+++ plaque is smaller
++ plaque half size
+ barely visible plaque
*some Toxoplasma seen upon microscopy Plaque number is given as a percentage of the matched DMSO control group.

We claim:

1. A method for treating toxoplasmosis in a mammal comprising the step of administering to said mammal a therapeutically effective amount of the compound

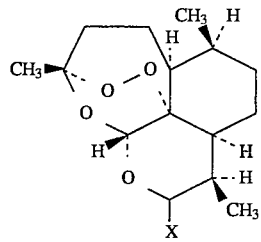

where X is OR, where R is a straight chain or branched alkyl having 1–6 carbons, whereby the growth of the organism causing toxoplasmosis is inhibited.

2. The method according to claim 1 wherein R is $CH_3$.

3. The method according to claim 1 wherein R is $CH_2CH_3$.

4. The method according to claim 1 wherein the compound is i-propyl-ether-artemisinin.

5. The method according to claim 1 wherein the compound is i-butyl-ether-artemisinin.

6. The method according to claim 1 wherein the compound is sec-butyl-ether-artemisinin.

7. A method for inhibiting growth of parasites of the suborder Eimeriorina wherein said parasites have a defined life cycle similar to Toxoplasma which comprises application to a growth environment of said parasite comprising a mammalian host an amount of a compound effective for inhibition of growth of said parasite wherein said compound has the formula

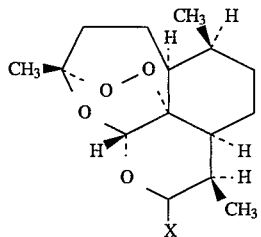

where X is OR, where R is a straight chain or branched alkyl having 1–6 carbons.

8. A method according to claim 7 wherein the parasites are selected from the genera Eimeria, Cryptosporidium, Isospora, and Sarcocystis.

9. A method according to claim 7 wherein the parasites are selected from the genera Eimeria, Cryptosporidium, and Isospora.

10. A method according to claim 7 wherein the genus is Toxoplasma.

11. The method according to claim 7 wherein R is $CH_3$.

12. The method according to claim 7 wherein R is $CH_2CH_3$.

* * * * *